(12) United States Patent
Liang

(10) Patent No.: US 12,194,021 B2
(45) Date of Patent: Jan. 14, 2025

(54) MODIFIED HERBAL COMPOSITIONS FOR NEUROMODULATION

(71) Applicant: University of Southern California, Los Angeles, CA (US)

(72) Inventor: Jing Liang, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 17/728,041

(22) Filed: Apr. 25, 2022

(65) Prior Publication Data

US 2022/0387379 A1 Dec. 8, 2022

Related U.S. Application Data

(60) Provisional application No. 63/192,391, filed on May 24, 2021.

(51) Int. Cl.

| | | |
|---|---|---|
| A61K 31/353 | (2006.01) | |
| A61K 31/198 | (2006.01) | |
| A61K 31/4045 | (2006.01) | |
| A61K 31/585 | (2006.01) | |
| A61K 36/35 | (2006.01) | |
| A61K 36/534 | (2006.01) | |
| A61K 36/575 | (2006.01) | |
| A61K 36/725 | (2006.01) | |
| A61K 36/752 | (2006.01) | |
| A61K 36/81 | (2006.01) | |
| A61K 36/84 | (2006.01) | |
| A61P 25/00 | (2006.01) | |
| A61P 25/20 | (2006.01) | |

(52) U.S. Cl.
CPC .......... *A61K 31/353* (2013.01); *A61K 31/198* (2013.01); *A61K 31/4045* (2013.01); *A61K 31/585* (2013.01); *A61K 36/35* (2013.01); *A61K 36/534* (2013.01); *A61K 36/575* (2013.01); *A61K 36/725* (2013.01); *A61K 36/752* (2013.01); *A61K 36/81* (2013.01); *A61K 36/84* (2013.01); *A61P 25/00* (2018.01); *A61P 25/20* (2018.01)

(58) Field of Classification Search
None
See application file for complete search history.

(56) References Cited

U.S. PATENT DOCUMENTS

| | | | |
|---|---|---|---|
| 6,814,987 | B2 | 11/2004 | Stogniew et al. |
| 7,935,714 | B2 | 5/2011 | Chan et al. |
| 10,517,322 | B1 * | 12/2019 | Lee ........................ A23L 33/30 |
| 11,351,150 | B2 | 6/2022 | Rinaldi et al. |
| 2006/0198872 | A1 | 9/2006 | Ikonte et al. |
| 2008/0039526 | A1 | 2/2008 | Ozeki et al. |
| 2010/0120887 | A1 | 5/2010 | Terman et al. |
| 2011/0189161 | A1 | 8/2011 | Blum et al. |
| 2014/0141082 | A1 | 5/2014 | Gao |
| 2015/0071993 | A1 | 3/2015 | Patel et al. |
| 2015/0284667 | A1 | 10/2015 | Edman et al. |
| 2017/0216176 | A1 | 8/2017 | Chen |
| 2019/0231711 | A1 | 8/2019 | Weimann |
| 2020/0138783 | A1 * | 5/2020 | Rinaldi .................. A61K 33/08 |
| 2021/0113646 | A1 * | 4/2021 | Antony ................ A61K 36/185 |
| 2022/0257561 | A1 * | 8/2022 | Tejani .................... A61K 31/12 |

FOREIGN PATENT DOCUMENTS

| | | |
|---|---|---|
| AU | 2018292531 A1 | 2/2020 |
| CN | 108096445 A | 6/2018 |
| CN | 109965026 A | 7/2019 |
| CN | 110810693 A * | 2/2020 |
| EP | 1182257 B1 | 1/2005 |
| WO | 2019005962 A1 | 1/2019 |
| WO | 2020247961 A1 | 12/2020 |

OTHER PUBLICATIONS

Rempel, V., et al., Magnolia Extract, Magnolol, and Metabolites: Activation of Cannabinoid CB2 Receptors and Blockade of the Related GPR55, ACS Med. Chem. Lett. Apr. 1, 2013, 41-45 (Year: 2013).*
Machine translation of CN 110810693 A.*
Carneiro et al., "Vine Tea (*Ampelopsis grossedentata*): A Review of Chemical Composition, Functional Properties, and Potential Food Applications," J Funct Foods, 76:104317, Jan. 2021.
Carneiro et al., Erratum to "Vine Tea (*Ampelopsis grossedentata*): A Review of Chemical Composition, Functional Properties, and Potential Food Applications," J Funct Foods, 76:104317, Jan. 2021.
Hu et al., "New Method for Extracting and Purifying Dihydromyricetin from Ampelopsis grossedentata," ACS Omega, 5 (23):13955-13962, Jun. 2020.
International Preliminary Report on Patentability of the International Bureau of WIPO in PCT/US2020/036714, dated Dec. 7, 2021; 7pgs.
Liu et al., "Dihydromyricetin: A Review on Identification and Quantification Methods, Biological Activities, Chemical Stability, Metabolism and Approaches To Enhance Its Bioavailability," Trends Food Sci Technol., 91:586-597, Sep. 2019.
White et al., "Chapter 14 Natural Withanolides in the Treatment of Chronic Diseases," Adv Exp Med Biol., 928:329-373, Sep. 2016.

(Continued)

*Primary Examiner* — H. Sarah Park
(74) *Attorney, Agent, or Firm* — Haukaas Fortius PLLC; Michael Haukaas

(57) ABSTRACT

Herbal compositions comprising dihydromyricetin (DHM) and methods of use. The herbal compositions include DHM in combination with other ingredients to form compositions that can significantly improve the quality and duration of sleep, reduce the time for onset of improved sleep quality and duration, and treat or alleviate the symptoms of sleep-related disorders and neurological conditions. The composition is a therapeutic alternative to drugs to alleviate sleep disorders and related symptoms and ailments.

13 Claims, 7 Drawing Sheets

(56) References Cited

OTHER PUBLICATIONS

International Search Report and Written Opinion of the ISA/US dated Aug. 16, 2022 in International Application No. PCT/US2022/030545; 10pgs.

Buerger et al., "CSF tau protein phosphorylated at threonine 231 correlates with cognitive decline in MCI subjects", Neurology Aug. 2002; 59:627-629.

Milà-Alomà et al., "Plasma p-tau231 and p-tau217 as state markers of amyloid-β pathology in preclinical Alzheimer's disease" Nature Medicine, Sep. 2022, vol. 28, pp. 1797-1801.

Suárez-Calvet et al., "Novel tau biomarkers phosphorylated at T181, T217, or T231 rise in the initial stages of the preclinical Alzheimer's continuum when only subtle changes in Aβ pathology are detected", EMBO Molecular Medicine, Nov. 2020, 12: e12921, 19pgs.

* cited by examiner

MODIFIED HERBAL COMPOSITIONS FOR NEUROMODULATION

RELATED APPLICATIONS

This application claims priority under 35 U.S.C. § 119(e) to U.S. Provisional Patent Application No. 63/192,391 filed May 24, 2021, which is incorporated herein by reference.

GOVERNMENT SUPPORT

This invention was made with government support under Grant No. AA017991 awarded by the National Institutes of Health. The government has certain rights in the invention.

BACKGROUND OF THE INVENTION

Trouble sleeping is a problem that afflicts many people. A good night's sleep has become a luxury. Statistically, 4 out of 10 people have insomnia. To sleep well, many people choose to take sleeping pills. Unfortunately, sleeping pills are damaging to the body, and both tolerance and addiction are easily developed. To avoid these negative consequences, many people prefer taking herbal remedies. Herbal remedies are consumed by approximately 50% of the population in the United State for health and wellness, including products promoted for sleep problems and mental health issues. However, a product that has a high efficacy for sleep, is safe for human use, and that minimizes side effects without addiction is currently unavailable.

SUMMARY

The present technology provides compositions (e.g., dietary supplements) and methods for improving sleep and for the safe treatment of sleep disorders. The compositions include dihydromyricetin (DHM), a bioflavonoid extracted from *Hovenia* or Rattan tea (vine), that has been used in traditional medicines to treat fever and parasitic infections. However, DHM has several undesirable properties including low solubility, as well as degradation and oxidation after exposure to air, light, and high temperatures. Hence the present technology also provides new forms and formulations of DHM that address these issues as well.

Thus, the present technology provides an herbal composition comprising DHM or a salt or complex thereof, and one or more of ashwagandha extract, valerian extract, magnolia extract, jujube extract, lemon balm, and L-theanine. In some embodiments, the herbal composition comprises melatonin.

The present technology also provides compositions comprising synthetic DHM and/or one or more herbal extracts including *Hovenia* extract or vine tea extract. The composition can include melatonin and one or more forms of vitamin B and folic acid.

The DHM or *Hovenia* extract can be stabilized to chemical degradation and its aqueous solubility can be enhanced compared to an unformulated DHM, vine tea extract, or *Hovenia* extract. Additionally, the present technology provides a method for treating a subject in need of neuromodulation comprising administering to the subject an effective amount of a composition disclosed herein.

The compositions of the present technology can be used as supplements, as nutraceuticals, or they can be used in medical therapy. The medical therapy can be treating insomnia, sleep disorders, anxiety, reduced cognition, impaired memory, and neurodegenerative diseases. The present technology also provides for the use of a composition as described herein for the manufacture of a medicament to treat a condition or disease in a mammal, for example, insomnia, anxiety, or neurodegeneration in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
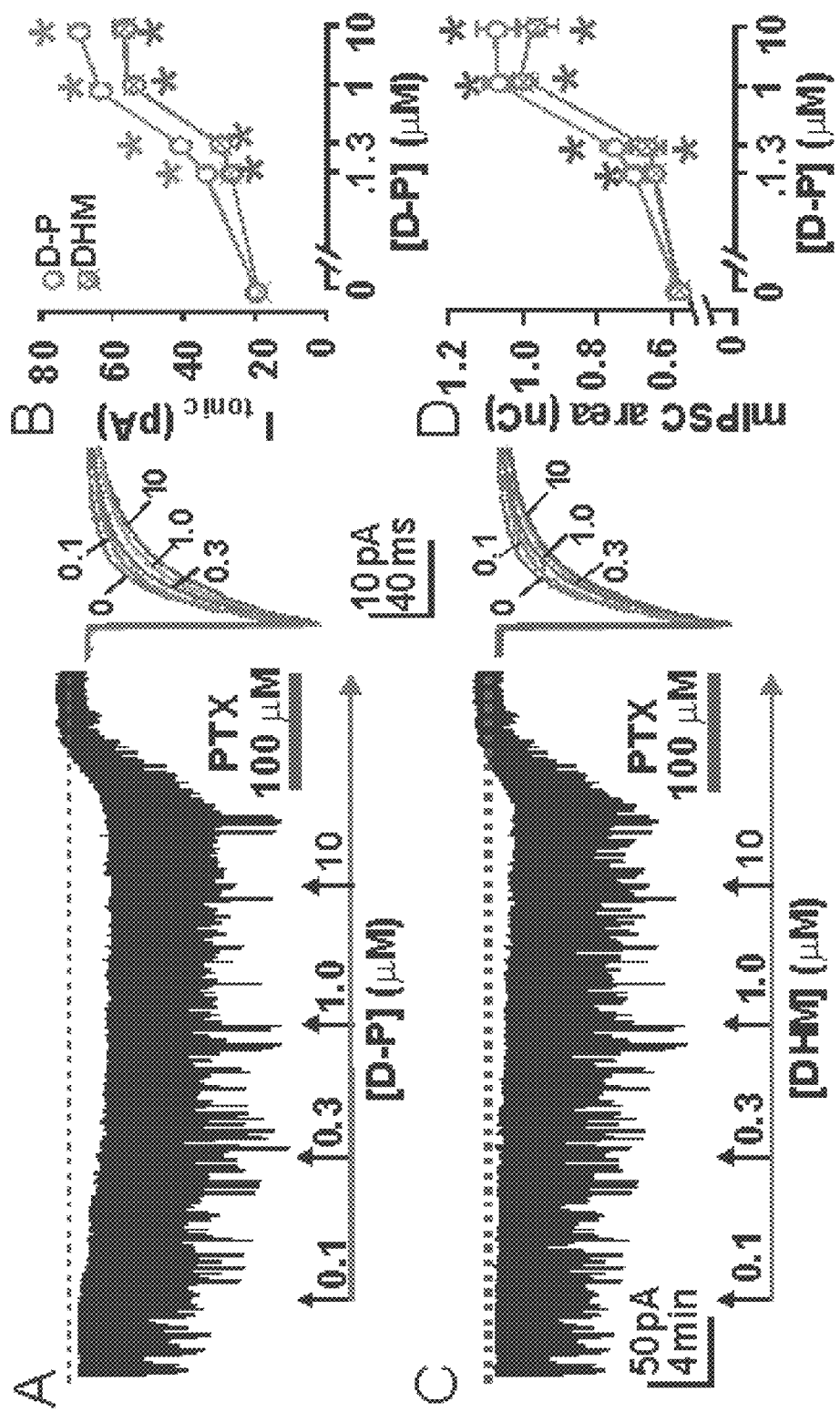
FIG. 1. OHM is a positive modulator of $GABA_ARs$. Recordings were whole cell voltage-clamped at −70 mV. A, C, recording from hippocampal DGCs (left panel) in slices, and superimposed averaged mIPSCs (right panel). B, D Summary of $1_{tonic}$ and mIPSC area potentiated by a DHM-Piperidine Complex (D-P) and DHM from 0.1 to 30 μM (n=6 neurons/3 rats).

The present technology provides an herbal composition comprising a DHM source (synthetic DHM, an extract containing DHM, or a salt thereof) such as vine tea extract, and one or more of ashwagandha extract, valerian extract, magnolia extract, jujube extract, lemon balm, and L-theanine. In some embodiments, the DHM can be in the form of a DHM salt or complex. Based on our systematic study on DHM, we modified DHM's physicochemical properties, such as efficacy, solubility, hygroscopicity and stability, for example, through salt formation with natural amino acids, or compositions with amino compounds, vitamins, and other natural compounds. The generated compositions of DHM display enhanced efficacy, solubility, and potency for enhanced sleep onset, total sleep time, and sleep quality. The present technology thus provides a general approach for the development of DHM compositions having enhanced properties.

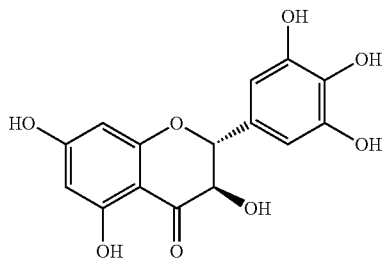

Dihydromyricetin (DHM)

Chemical Formula: $C_{15}H_{12}O_8$

Molecular Weight: 320.25

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph. When a value recited being associated with a ±variation, the upper (+) and lower (−) variations are each explicitly and separately envisions as specific variations of the particular element, each in combination with all other embodiments referenced herein.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, nutritional, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of a compound of the disclosure into a subject by a method or route that results in at least partial localization of the compound to a desired site. The compound can be administered by any appropriate route that results in delivery to a desired location in the subject.

The compound and compositions described herein may be administered with additional compositions to prolong stability and activity of the compositions, or in combination with other supplements, nutraceuticals, therapeutics, or drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

Embodiments of the Technology

The present technology provides a composition comprising a DHM source (such as synthetic DHM or an extract containing DHM) such as *Hovenia* extract, vine tea extract, and/or rattan tea extract, and ashwagandha extract, valerian extract, magnolia extract, jujube extract, lemon balm, or L-theanine.

In one embodiment, the composition comprises dihydromyricetin (DHM), ashwagandha extract, and one or more of valerian extract, magnolia extract, jujube extract, lemon balm, and L-theanine, wherein a weight ratio of DHM to ashwagandha extract is about 3:2.

In another embodiment, the composition comprises dihydromyricetin (DHM), valerian extract, and one or more of ashwagandha extract, magnolia extract, jujube extract, lemon balm, and L-theanine, wherein a weight ratio of DHM to valerian extract is about 3:1.5.

In other embodiments, the composition comprises DHM or a salt or complex thereof, and one or more of ashwagandha extract, valerian extract, magnolia extract, jujube extract, lemon balm, and L-theanine, wherein a source of the DHM is synthetic or a natural herbal source. In some embodiments the source of DHM is natural herbal source and the source comprises *Hovenia* extract, vine tea extract, and/or rattan tea extract.

The terms synthetic DHM, natural or herbal DHM, *Hovenia* extract, vine tea extract, and rattan tea extract, (i.e., the sources of DHM) are interchangeable in various embodiments. In various embodiments the source of DHM is a combination of any two or more sources of DHM.

In some embodiments, the composition comprises synthetic DHM. In some embodiments, the composition comprises an extract containing DHM. The DHM can be in the form of a DHM salt or complex. The DHM salt or complex can include an alkyl amine or an amino acid. As used herein, alkyl amines include dialkyl amines, trialkyl amines, and cyclic amines. Examples of suitable alkyl amines and amino acids include piperidine, diethylamine, triethylamine, arginine, and lysine.

In various embodiments, the extract, such as, vine tea extract comprises about 80 wt. % or about 90 wt. % to about 100 wt. % DHM, or less than 100 wt. % DHM. In various embodiments, the vine tea extract comprises about 90 wt. % DHM or 98 wt. % DHM. In various embodiments, the composition includes about 5-40 wt. % DHM, about 5-30 wt. % DHM, about 5-27.5 wt. % DHM, about 5-25 wt. % DHM, about 10-20 wt. % DHM, about 20-30 wt. % DHM, about 30-40 wt. % DHM, or about 15 wt. % DHM.

In various embodiments, the composition comprises DHM or vine tea extract, and ashwagandha extract. In various embodiments, the ashwagandha extract comprises about 1 wt. % to about 10 wt. % withanolides, or about 10 wt. % to about 20 wt. % withanolides. In various embodiments, the ashwagandha extract comprises about 5 wt. % withanolides.

In various embodiments, the composition comprises DHM or vine tea extract, and valerian extract. In various embodiments, the composition comprises DHM or vine tea extract, and magnolia extract. In various embodiments, the composition comprises DHM or vine tea extract, and jujube extract. In various embodiments, the composition comprises DHM or vine tea extract, and lemon balm. In various embodiments, the composition comprises DHM or vine tea extract, and L-theanine. In various embodiments, the composition comprises DHM or vine tea extract, ashwagandha extract and valerian extract.

In various embodiments, a weight ratio of DHM or vine tea extract to ashwagandha extract is about 3:2. In various embodiments, a weight ratio of DHM or vine tea extract to valerian extract is about 3:1.5. In various embodiments, a weight ratio of DHM or vine tea extract to ashwagandha extract to valerian extract is about 3:2:1.5.

In various embodiments, the composition comprises DHM or vine tea extract, and ashwagandha extract, valerian extract, magnolia extract, jujube extract, lemon balm, and L-theanine. In various embodiments, a weight ratio of vine tea extract to ashwagandha extract to valerian extract to magnolia extract to jujube extract to lemon balm to L-theanine is about 3:2:1.5:1:1:1:2.

In various embodiments, the composition further comprises an extended time-release formulation of melatonin. In various embodiments, the composition further comprises melatonin, wherein the melatonin is not an extended time-release formulation of melatonin. In various embodiments, a weight ratio of vine tea extract to melatonin is about 100:1 or about 100:2, wherein the melatonin is an extended time-release formulation of melatonin. In various embodiments, a weight ratio of vine tea extract to melatonin is about 150:1 or about 150:2, wherein the melatonin is not an extended time-release formulation of melatonin.

In various embodiments, a serving of the herbal composition has about 300 mg or more of DHM, or at least 300 mg DHM. In various embodiments, a serving of the herbal composition has about 300 mg or more of vine tea extract, about 200 mg ashwagandha extract, about 150 mg valerian extract, about 100 mg magnolia extract, about 100 mg jujube extract, about 100 mg lemon balm, and about 200 mg L-theanine. In various embodiments, a serving of the herbal composition further comprises about 3 mg melatonin in an extended time-release formulation. In various embodiments, a serving of the herbal composition further comprises about 2 mg melatonin that is not in an extended time-release formulation.

In various embodiments, a serving of the herbal composition has 300 mg±15% DHM. In various embodiments, a serving of the herbal composition has 300 mg±15% vine tea extract, 200 mg±15% ashwagandha extract, 150 mg±15% valerian extract, 100 mg±15% magnolia extract, 100 mg±15% jujube extract, 100 mg±15% lemon balm, and 200 mg±15% L-theanine. In various embodiments, a serving of the herbal composition further comprises 3 mg±15% melatonin or 1±15% to 5 mg±15% melatonin in an extended time-release formulation. In various embodiments, a serving of the herbal composition further comprises 2 mg±15% melatonin or 1±15% to 5 mg±15% melatonin that is not in an extended time-release formulation.

In various embodiments, the herbal composition has a total weight of about 500 mg to about 2000 mg in a serving. In various embodiments, the herbal composition has a total weight of about 500 mg to about 2000 mg in a capsule or tablet. In various embodiments, a serving of the herbal composition is provided as 1-6 individual capsules or tablets. In various embodiments, a single serving of the herbal composition is equivalent to 1-6 individual capsules or tablets.

The present technology also provides an herbal composition comprising:
(a) DHM or one or more herbal extracts including *Hovenia* extract, vine tea extract, or rattan tea extract;
(b) one or more forms of vitamin B; and
(c) folic acid.

In some embodiments, the DHM, *Hovenia* extract, or rattan tea extract is stabilized to chemical degradation or photochemical degradation (e.g., air, oxygen, light) and/or its aqueous solubility is enhanced compared to unformulated DHM, *Hovenia* extract, or unformulated rattan tea extract.

In some embodiments, the composition comprises *Hovenia* extract, vine tea extract, or rattan tea extract, and magnolia vine extract, jujube kernel extract, and panax notoginseng extract. In some embodiments, the composition further comprises ashwagandha extract and/or valerian extract and/or L-theanine.

In various embodiments, the composition includes about 5-30 wt. % DHM (or *Hovenia* extract, vine tea extract, or rattan tea extract, wherever DHM is recited herein, or an equivalent amount of the active DHM), about 5-25 wt. % DHM, about 10-20 wt. % DHM, or about 15 wt. % DHM. In some embodiments, the weight percent of rattan tea extract is about 8% to about 15%. In some embodiments, the weight percent of magnolia vine extract, jujube kernel extract, and panax notoginseng extract are each independently about 3% to about 7%. In some embodiments, the weight percent of DHM (natural or synthetic), *Hovenia* extract, vine tea extract, or rattan tea extract is about 1% to about 4%.

In some embodiments, the composition comprises vitamin B1, vitamin B3, vitamin B6, and vitamin B12. In some embodiments, the weight percent of each vitamin B is independently about 0.005% to about 1%. In some embodiments, the weight percent of each vitamin B is independently about 0.05% to about 0.5%.

In some embodiments, the folic acid is in the form of vitamin B9. In some embodiments, the weight percent of folic acid is about 0.005% to about 0.05%.

Also, this disclosure provides a method for treating a subject in need of neuromodulation comprising administering to the subject an effective amount of an herbal composition described herein.

In some embodiments, the neuromodulation effectively aids insomnia, sleep, anxiety, cognition, memory, pain or pain from sleep disorders, or a combination of two or more thereof. In some embodiments, the neuromodulation effectively aids sleep compared to an untreated control group. In some embodiments, the neuromodulation effectively shortens the onset of sleep compared to an untreated control group. In some embodiments, the neuromodulation effectively aids total sleep time compared to an untreated control group. In some embodiments, the neuromodulation effectively aids sleep quality compared to an untreated control group. In some embodiments, the neuromodulation effectively aids sleep latency compared to an untreated control group. In some embodiments, the neuromodulation effectively aids wake after sleep onset compared to an untreated control group. In some embodiments, the neuromodulation effectively aids sleep efficiency compared to an untreated control group. In some embodiments, the neuromodulation effectively aids anxiety compared to an untreated control group.

In various embodiments the therapeutic effect of DHM is synergistic (or more than additive) with one or more of ashwagandha extract, valerian extract, magnolia extract, jujube extract, lemon balm, or L-theanine. In various embodiments the therapeutic effect of DHM is synergistic with ashwagandha extract. In various embodiments the therapeutic effect of DHM is synergistic with valerian extract.

In some embodiments, a serving of the herbal composition has about 300 mg or more DHM, *Hovenia* extract, rattan tea extract, or vine tea extract, about 200 mg ashwagandha extract, about 150 mg valerian extract, about 100 mg magnolia extract, about 100 mg jujube extract, about 100 mg lemon balm, about 200 mg L-theanine, optionally about 3 mg melatonin in an extended time-release formulation, and optionally about 2 mg melatonin that is not in an extended time-release formulation.

In some embodiments, a serving of the herbal composition has 300 mg±15% DHM or vine tea extract, 200 mg±15% ashwagandha extract, 150 mg±15% valerian extract, 100 mg±15% magnolia extract, 100 mg±15% jujube extract, 100 mg±15% lemon balm, 200 mg±15% L-theanine, optionally 3 mg±15% melatonin in an extended time-release formulation, and optionally 2 mg±15% melatonin that is not in an extended time-release formulation.

In some embodiments, the effective amount is a serving of the herbal composition administered as 1-6 individual capsules or tablets, wherein each capsule or tablet has a total weight of about 500 mg to about 2000 mg of the composition.

In some embodiments, the composition comprises about 2.5 wt. % DHM or *Hovenia* extract, about 10 wt. % or about 12.5% rattan tea extract, about 5 wt. % magnolia vine extract, about 5 wt. % jujube kernel extract, and about 5 wt. % panax notoginseng extract. In some embodiments, the DHM or *Hovenia* extract, rattan tea extract, magnolia vine extract, jujube kernel extract, and panax notoginseng extract is about 25 wt. % to about 35 wt. % of the composition. In various embodiments, the composition includes about 5-30 wt. % DHM, about 5-25 wt. % DHM, about 10-20 wt. % DHM, or about 15 wt. % DHM.

In some embodiments, the composition comprises about 0.05 wt. % vitamin B1, about 0.5 wt. % vitamin B3, about 0.05 wt. % vitamin B6, about 0.01 wt. % folic acid, and about 0.1 wt. % vitamin B12. In some embodiments, the vitamin B1, vitamin B3, vitamin B6, folic acid, and vitamin B12 is about 0.5 wt. % to about 1 wt. % of the composition.

In various embodiments, the effective amount administered is an oral dose of about 0.5 grams to about 3 grams of the composition. In some embodiments, the effective amount administered is about 0.1 grams, about 0.5 grams, about 1 gram, about 1.5 grams, about 2 grams, about 2.5 grams, about 3.0 grams, about 3.5 grams, about 4 grams, or any amount between the recited amounts.

In some embodiments, the DHM, *Hovenia* extract, rattan tea extract, or vine tea extract in the composition is stabilized to degradation by air or oxygen compared to unformulated DHM, *Hovenia* extract, rattan tea extract, or vine tea extract.

In various embodiments, the composition does not include one or more of gelatin, titanium dioxide, and food coloring.

Dietary Supplement and Nutraceutical Formulations

The compounds, extracts, and compositions described herein can be used to prepare supplements, nutraceuticals, and therapeutic compositions, for example, by combining the compound, extract, or composition with food or with an acceptable diluent, excipient, or carrier. The compounds or extracts may be added to a carrier in the form of a salt or solvate. For example, in cases where compounds are sufficiently basic or acidic to form stable nontoxic acid or base salts, administration of the compounds as salts may be appropriate. Examples of acceptable salts are organic acid addition salts formed with acids that form a physiologically acceptable anion, for example, tosylate, methanesulfonate, acetate, citrate, malonate, tartrate, succinate, benzoate, ascorbate, $\alpha$-ketoglutarate, and $\beta$-glycerophosphate. Suitable inorganic salts may also be formed, including hydrochloride, halide, sulfate, nitrate, bicarbonate, and carbonate salts.

Salts and complexes may be obtained using standard procedures well known in the art, for example by reacting a sufficiently basic compound such as an amine with a suitable acid to provide a physiologically acceptable ionic compound. Alkali metal (for example, sodium, potassium, or lithium) or alkaline earth metal (for example, calcium) salts of carboxylic acids or amino acids can also be prepared by analogous methods.

The compositions described herein can be formulated as supplements or nutraceutical compositions and administered to a mammalian host, such as a human patient, in a variety of forms. The compositions can be specifically adapted to oral administration.

The compositions described herein may be administered in combination with a pharmaceutically acceptable vehicle, such as an inert diluent or an assimilable edible carrier. For oral administration, compositions can be enclosed in hard- or soft-shell gelatin capsules, compressed into tablets, or incorporated directly into the food of a patient's diet. Compositions may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

The ultimate dosage form should be sterile and stable under the conditions of manufacture and storage. A liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride.

Useful solid carriers include finely divided solids such as talc, clay, microcrystalline cellulose, silica, alumina, and the like. Useful liquid carriers include water, dimethyl sulfoxide, alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be taken orally or by other effective means.

Thickeners such as synthetic polymers, fatty acids, fatty acid salts and esters, fatty alcohols, modified celluloses, or modified mineral materials can be included in the formulations.

Useful dosages of the compositions described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound is conveniently formulated in unit dosage form; for example, containing 5 to 1000 mg, conveniently 10 to 750 mg, most conveniently, 50 to 500 mg of active ingredient per unit dosage form. In one embodiment, the present technology provides a composition comprising at least 100 mg of DHM per dosage form. The desired total daily dose may conveniently be presented in a single dose or as divided doses administered at appropriate intervals, for example, as two, three, or four sub-doses per day. The sub-dose itself may be further divided, e.g., into a number of discrete loosely spaced administrations.

The compositions described herein can be effective agents for insomnia, anxiety and cognition and have higher potency and/or reduced toxicity as compared to an unformulated DHM or *Hovenia* extract. The ability of a compositions to treat insomnia, anxiety and cognition may be determined by using assays well known to the art.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Representative Procedure of Salt-formulations with DHM

DHM (1.6 g, 5.0 mmol, HPLC grade, 99%. Master Herbs LLC. Los Angeles, USA) was dissolved in MeOH (20 mL) at room temperature for 30 min and then was cooled in an ice bath. To prepare this mixture, a solution of nature amino acid (Arginine or Lysine) (10 mmol) or amino compounds (diethylamine, piperidine or triethylamine) in MeOH was added dropwise at −10° C. under argon and then was allowed to warm to room temperature. After the reaction was completed, the resulting mixture was concentrated under reduced pressure to give a residue. The residue was filtered and washed by MeOH 3 times to provide the desired product (Scheme 1).

DHM-Piperidine Complex: piperidin-1-ium (2R,3R)-2-(3,4-dihydroxy-5-oxidophenyl)-3,5-dihydroxy-4-oxochroman-7-olate (MW: 405.40).

DHM-Diethylamine Complex: diethylammonium (2R,3R)-2-(3,4-dihydroxy-5-oxidophenyl)-3,5-dihydroxy-4-oxochroman-7-olate (MW: 393.39).

DHM-Triethylamine Complex: triethylammonium (2R,3R)-2-(3,4-dihydroxy-5-oxidophenyl)-3,5-dihydroxy-4-oxochroman-7-olate (MW: 623.83).

DHM-Arg Complex: (S)-amino((4-amino-4-carboxybutyl)amino)methaniminium (2R,3R) (3,4-dihydroxy-5-oxidophenyl)-3,5-dihydroxy-4-oxochroman-7-olate (MW: 1017.07).

DHM-Lys Complex: (S)-5-amino-5-carboxypentan-l-aminium (2R,3R)-2-(3,4-dihydroxy oxidophenyl)-3,5-dihydroxy-4-oxochroman-7-olate (MW: 466.44).

Scheme 1. Salt-forms of DHM

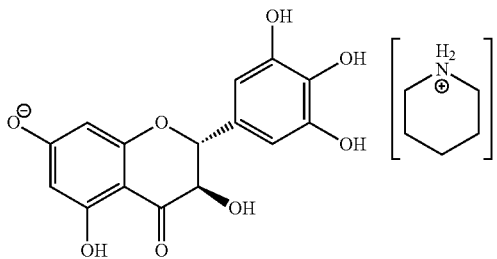

DHM-Piperidine Complex
$C_{20}H_{23}NO_8$
MW: 405.40

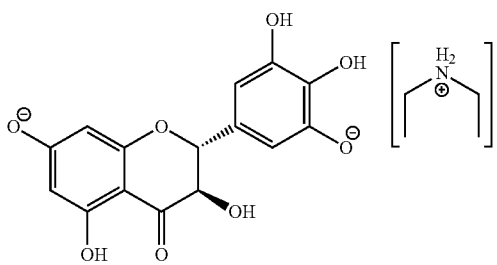

DHM-Diethylamine Complex
$C_{19}H_{23}NO_8$
MW: 393.39

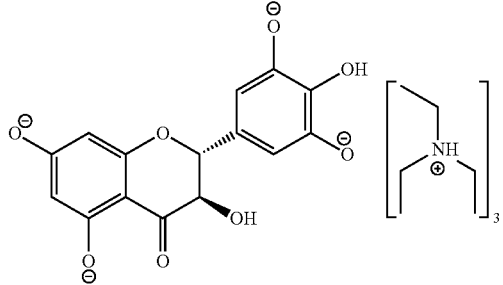

DHM-Triethylamine Complex
C$_{33}$H$_{57}$N$_3$O$_8$
MW: 623.83

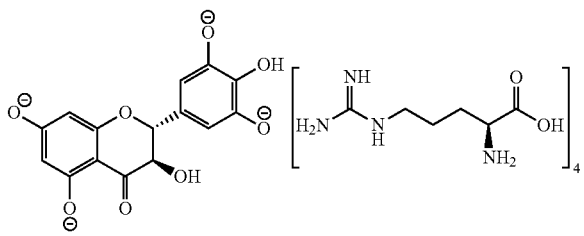

DHM-Arg Complex
C$_{39}$H$_{68}$N$_{16}$O$_{16}$
MW: 1017.07

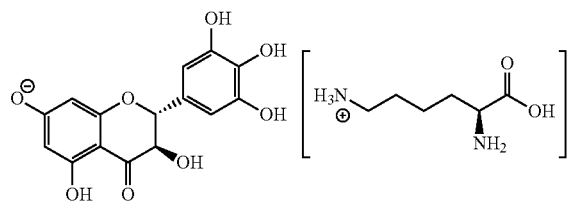

DHM-Lys Complex
C$_{21}$H$_{26}$N$_2$O$_{10}$
MW: 466.44

Example 2. Methods

1) The Representative Procedure of salt-formulations. DHM (1.6 g, 5.0 mmol, HPLC grade, 99%. Master Herbs LLC. Los Angeles, USA) was dissolved in MeOH (20 mL) at room temperature for 30 min and then was cooled in an ice bath. To this prepared mixture, a solution of nature amino acid (Arginine or Lysine) (10 mmol) or amino compounds (diethylamine, piperidine or triethylamine) in MeOH was added dropwise at −10° C. under argon and then was allowed to warm to room temperature. After the reaction was completed, the resulting mixture was concentrated under reduced pressure to give a residue. The residue was filtered and washed by MeOH 3 times to provide the desired product.

2) Whole-Cell Patch-Clamp Recordings from Brain Slices. Transverse slices (400 lm) of dorsal hippocampus were obtained from wt and TG-SwDI mice (male, 20 months old) using a vibratome (VT 100; Technical Products International). Slices were perfused continuously with artificial CSF (ACSF) composed of the following (in mM): 125 NaCl, 2.5 KCl, 2 CaCl$_2$, 2 MgCl$_2$, 26 NaHCO$_3$, and 10 D-glucose. The ACSF was bubbled continuously with 95% O2/5% CO2 to ensure adequate oxygenation of slices and a pH of 7.4 and kept at 34±0.5° C. for perfusion. TTX (0.5 μM), APV (40 μM), CNQX (10 μM), and CGP54626 (1 μM, GABABR antagonist) were added to ACSF to pharmacologically isolate GABAAR-mediated mIPSCs. Patch electrodes were filled with internal solution containing the following (in mM): 137 CsCl, 2 MgCl$_2$, 1 CaCl$_2$, 11 EGTA, 10 HEPES, and 3 ATP, pH adjusted to 7.30 with CsOH. Recordings targeted dentate gyms granule cells (DGCs) of hippocampal slices [36]. Voltage-clamp whole-cell recording was performed using a patch clamp amplifier 3) EPM: All animals were tested anxiety levels on EPM. Animals were placed on the central area of the maze, tested for 5 min and video recorded. The following measures were scored: number of entries into open arms, closed arms, or center platform and time spent in each of these areas. Data were reported as % of number of entries in arms, % of time spent in different entries, and number of total entries.

3) Gephyrin level measurement: Gephyrin amounts in control (group housing), AD, and AD+D-P group were determined. All mice brains were taken and prepared for assays. SDS-PAGE and Western blot analysis. Proteins were separated on SDS-polyacrylamide gels (Sigma) using the Bio-Rad Mini-Protean 3 cell system. Proteins were transferred on a polyvinylidene difluoride (PDVF) membrane (Sigma) and blocked with 4% non-fat dry milk. Blots were incubated overnight at 4° C. with rabbit anti-gephyrin (Santa Cruz, 1:200) and mouse anti-β-actin (Sigma, 1:1000), followed by HRP-conjugated secondary antibodies (1:5000)

for two hours at room temperature. Bands were detected using ECL detection kit (Sigma) and exposed to X-ray films. Bands were analyzed by densitometry using ImageQuant5.2 (Molecular Dynamics), normalized to the corresponding β-actin signal and compared.

4) Memory Test Protocol. Novel Object Recognition (NOR): Day 1-3: Habituation (once/day). Top open containers (open field) were used with video camera to record animal behavior. An animal was put into a container with no objects for 5 min. Context remained the same for each animal.

Day 4, Familiarization: Two identical objects (toys-FO: familiar object) were put into the container at specific positions. Then animals were put into the container to explore the objects for 5 min. Retention Trial 1.5 h: Each animal was placed in its home cage for 1.5 h after the familiarization. One of the toys was replaced with a new toy (NO, novel object and very different from FO). Then we put an animal into the container with the objects for 3 min and videotaped it for offline scoring. The score was based on how long animals spent exploring each toy. The pair of objects in a set was tested previously to avoid the natural preference of the mice for shape or light reflection; we used 4 sets of objects in total for this test.

Day 5, Retention Trial 24 h: We placed another new toy (NO) along with an original object (FO) in the container. Then we put an animal into the container and tested it for 3 min. We scored the animal behavior offline according to how long the animal spent exploring each object. The Object Recognition Index (ORI) was calculated, such that ORI=(tn−tf)/(tn+tf), where tf and tn represent times of exploring the familiar and novel objects, respectively.

Novel context recognition (NCR): Day 1-3 was Habituation (once/day). Two contexts (containers) A and B with similar field area were very different in shape. Context A was a rectangular, Context B was a circular container. The containers were open at the top with bedding to minimize stress and with video camera on top to record animal behavior. Each animal was placed in Context A without toys for 5 min, then back to home cage for 30 min. Then the animal was placed in Context B without toys for 5 min.

Day 4 was for Familiarization: Two different sets of toys were used as the familiar objects referred to as FO1 and FO2 respectively. Each set consists of two identical toys while FO1 and FO2 were very different in shape. The two toys of FO1 were each placed in a specific position in Context A. Each animal was placed in Context A and allowed to explore FO1 for 5 min; then animal was back to home cage for 30 min. The two toys of FO2 were each placed in a specific position in Context B. Each animal was placed in Context B and allowed to explore FO2 for 5 min.

Day 5 (24 h from familiarization): Retention Trials was performed to determine the memory retention of each animal for familiarized objects. One toy of FO1 in Context A was exchanged with one toy from FO2. Then each animal was allowed to explore the objects in Context A for 3 min. The test was videotaped and analyzed offline. The time spent exploring the familiar object (FO1) and exchanged object (FO2) were calculated where exploration equals touching the object with nose or paws or sniffing within 1.5 cm of the object. Recognition Index (RI) was calculated with formula; Index=(tn−tf)/(tn+tf), where tf represents the time of exploring the familiar object previously encountered in the same context and tn represents the time of exploring the object in a different context. Increased exploration of the object presented in a different context over the object previously encountered in the same context was interpreted as increased formation of contextual memory.

5) Locomotor assay: To measure the locomotor activity, the numbers of total entries were measured for each animal. Statistical differences were determined using ANOVA. These experiments will determine the effects of D-P on anxiety levels.

6) The elevated plus maze assay (EPM) was performed in a quiet and dark room with only a low power red light. Rats were placed on the central area of the maze, and their behavior video recorded for 5 min. The number of entries into open arms, closed arms, or center platform and time spent in each of these areas were scored during off-line analysis. Data were reported as % of number of entries in arms, % of time spent in different arms, and number of total entries.

Alternatively, the elevated plus maze for mice can consist of two opposing open (24×8 cm) and two enclosed arms (24×8×25 cm) connected by a central platform forming the shape of a plus sign. The dimensions of the central field which connects the open and closed arms are 8×8 cm. The plus maze was elevated to a height of 50 cm. Each mouse was immediately placed in the central square of the apparatus with the head facing one of the closed arms. Mice behavior during 5 min was observed and recorded by means of a video camera (Canon Digital, Japan), which was fixed to the wall above the elevated plus maze. In this test, the following parameters were detected and calculated: the number of entries (open arm entries and closed arm entries), % of open arm entries, and % of time spent in open arms.

Example 3. Evaluation of Dihydromyricetin Formulations

DHM-Piperidine Complex (D-P), can be dissolved into water and potentiate $GABA_ARs$ at 0.1 μM lower concentration, compared with natural DHM. To evaluate whether DHM-Piperidine Complex (D-P) can still potentiate GABAARs, whole-cell voltage-clamped recordings from hippocampal DGCs in slices were performed to test D-P and compared with DHM effects on GABAergic tonic current ($I_{tonic}$) and miniature inhibitory postsynaptic currents (mIPSCs). As FIG. 1 shows, we applied the dosages of D-P and DHM at concentration of 0.1, 0.3, 1.0, and 10 μM respectively. Compared with DHM enhancing GABAergic $I_{tonic}$ from 20 pA (basal $I_{tonic}$)→28 pA→31 pA→52 pA→55 pA, D-P enhancing GABAergic $I_{tonic}$ from 20 pA (basal $I_{tonic}$)→35 pA→42 pA →65 pA→70 pA (Table 1). The results indicate that the salt-form DHM, DHM-Piperidine Complex, can maintain DHM bioavailability, increase its efficacy, and improve water solubility.

TABLE 1

Evaluation of D-P effects compared with DHM.

| | Effects | 0 | 0.1 | 0.3 | 1 | 10 (μM) |
|---|---|---|---|---|---|---|
| DHM | $I_{tonic}$ | 20 | 28 (40%)* | 31 (55%)* | 52 (160%)* | 55 (175%)* |
| | mIPSCs | 100% | 5.0% | 13.3% | 58.3%* | 53.3%* |
| D-P | $I_{tonic}$ | 20 | 35 (75%)* | 42 (110%)* | 65 (225%)* | 70 (250%)* |
| | mIPSCs | 100% | 16.7%* | 23.3%* | 100.0%* | 133.3%* |

DHM-Piperidine Complex (D-P) can replicate DHM effects to restore expression of gephyrin in TG animals. We previously reported that DHM restores impaired GABAergic inhibitory transmission in TG mouse models through restore gephyrin, a postsynaptic GABA$_A$R anchor protein that regulates the formation and plasticity of GABAergic synapses, in TG-mice (Liang et al., 2014, Neurochemical Research. 39(6):1171-81). In this evaluation study, we repeated previous methods to test DHM-Piperidine Complex effects.

Figure 2:
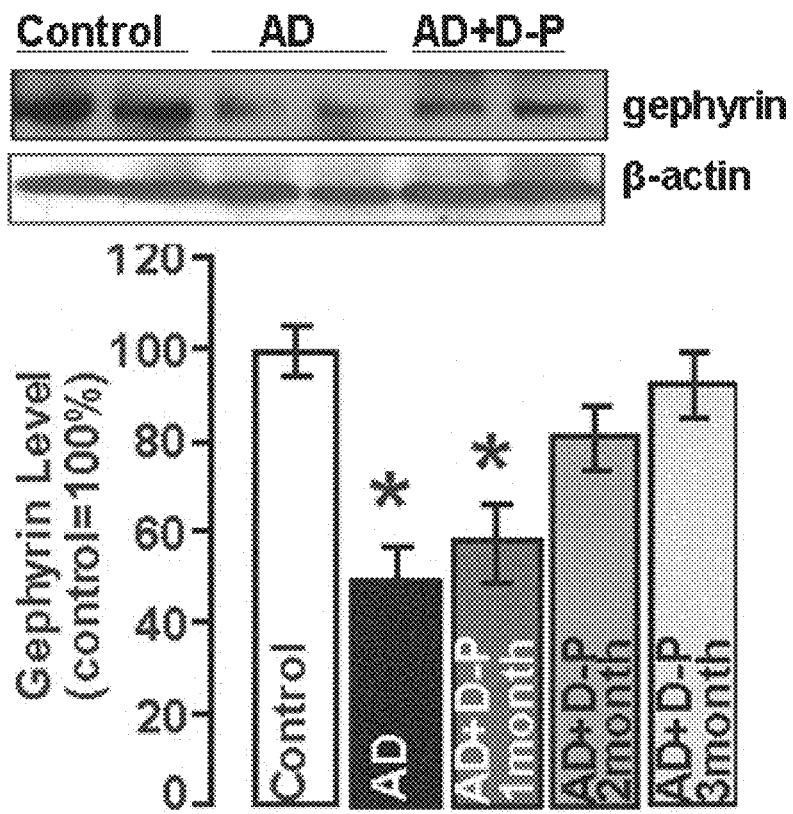
FIG. 2. DHM-Piperidine Complex (D-P) reverses reduced gephyrin levels in AD.

Gephyrin is the key scaffolding protein that organizes the inhibitory postsynaptic receptor density involving GABA$_A$R clustering at postsynaptic sites. Gephyrin not only has a structural function at GABAergic synaptic sites, but also plays a crucial role in synaptic dynamics. Therefore, we examined the protein levels of gephyrin in the hippocampus (left) and cortex (right) in the TG-mice and in D-P treated TG-mice compared to wt control. Western blot analysis showed that gephyrin levels of TG-mice were decreased compared to wt-control (FIG. 2). After 1 month D-P (1 mg/kg, oral daily) treatment, gephyrin levels partly recovered, while after 3 months of D-P treatment, gephyrin was restored to control levels. The reduced gephyrin levels in TG-mice may result in less synaptic clustering of GABAARs which could play a role in impaired GABAergic inhibitory neurotransmission. As a consequence, TG-mouse models exhibit loss of cognition and memory, lack of exploratory/locomotor activities, increased anxiety, and seizure susceptibility.

The results indicate that D-P treatment can restore gephyrin levels, which is a mechanism underlying the therapeutic effects of D-P on behavioral changes and improvement in learning and cognition functions in TG animal models of AD.

DHM-Piperidine Complex (D-P) can replicate DHM effects to improve cognition/memory impairment in TG-mice. We demonstrated that TG mice show signs of reduced cognitive memory. These abnormal behavioral changes are consistent with human studies and are commonly seen in AD patients. In this evaluation study, we repeated previous methods to test D-P effects.

Figure 3:
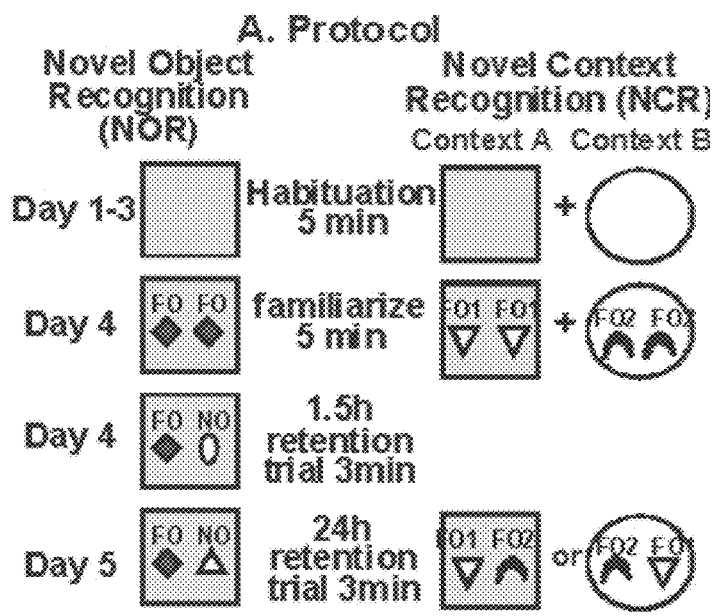
FIG. 3. D-P improves novel object cognition and novel context cognition in transgenic (TG)-mice. A. Memory Test Protocol. B. Novel object cognition. C. Novel context cognition test. D-P treatment for TG-mice improved cognition/memory compared with age-matched, sucrose treated TG-mice (n=6/group), **p<0.001, a one-way ANOVA followed by post hoc multiple comparison Tukey method.
Figure 3:
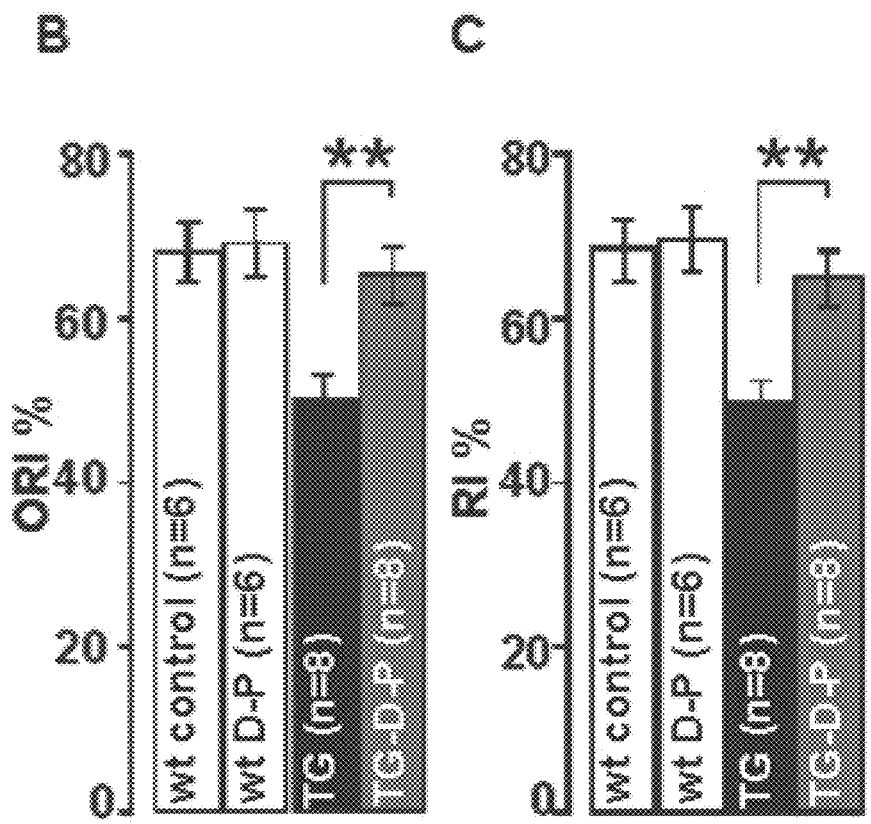

Mice were divided into four groups: (1) C57BL/6 wt male mice were treated with oral administration of 2% sucrose; (2) C57B1/6 wt male mice with oral administration of 1 mg/kg D-P in 2% sucrose; (3) TG-mice with oral administration of 2% sucrose; and (4) TG-mice with 1 mg/kg D-P in 2% sucrose. After 3 months of treatment, the cognition memory of mice was evaluated with NOR tests (FIG. 3B). The wt control spent more time exploring the novel objects (ORI=68.9±6.8%). ORI was reduced to 51.2±3.6% in TG-mice. The wt mice treated with D-P exhibited recognition similar to the wt control. D-P significantly improved NOR (ORI=70.1±6.8%) in TG-mice. Next, we evaluated NCR (FIG. 3C). The RI was calculated. Compared with the wt control, the TG-mice exhibited reduced RI (49.2±2.6%). D-P treatment reversed the RI in TG-mice and showed significant contextual memory improvement. These results indicate that daily oral application of D-P could replicate DHM effects and improve cognition memory in the TG-mice of AD.

DHM-Piperidine Complex (D-P) can replicate DHM effects to improve behavioral impairment in TG-mice. We examined the effect of D-P on AD symptom-like behavior in aged TG2576 mice compared with age-matched wt mice. Mice were divided into three groups: (1) C57BL/6 wt male mice (2% sucrose, oral administration), (2) TG-mice (2% sucrose, oral administration), and (3) TG-mice with D-P (2 mg/kg in 2% sucrose), respectively. After 3 months of treatment, mice were examined with behavioral assays.

Figure 4:
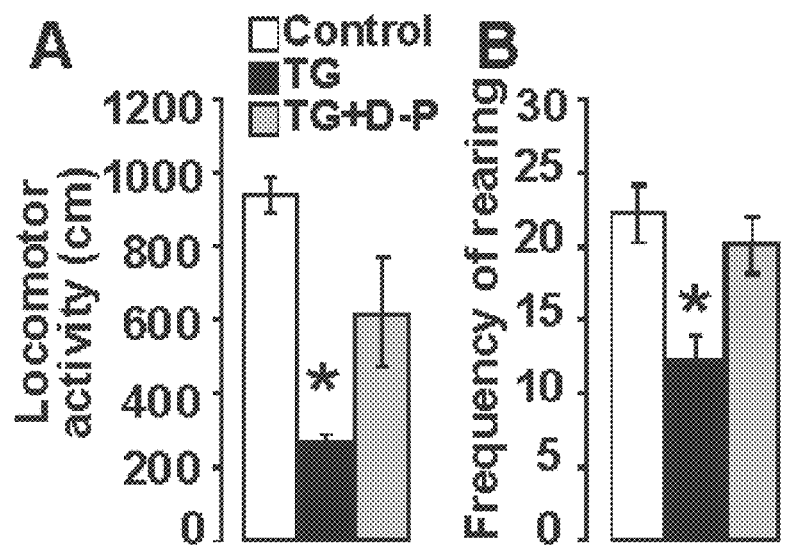
FIG. 4. D-P treatment improves locomotor activity and reduces anxiety in TG-mice. Open field was used to measure locomotor activity. A. Distance of movement. B. Frequency of rearing. C. Duration staying in the center. TG-mice showed inferred performance compared to wild-type (wt) control (n=8 mice). D-P treatment improved restored performance in TG-mice. D. Anxiety in wt control, TG, and TG+D-P mice was measured by EPM (n=7 per group).
Figure 4:
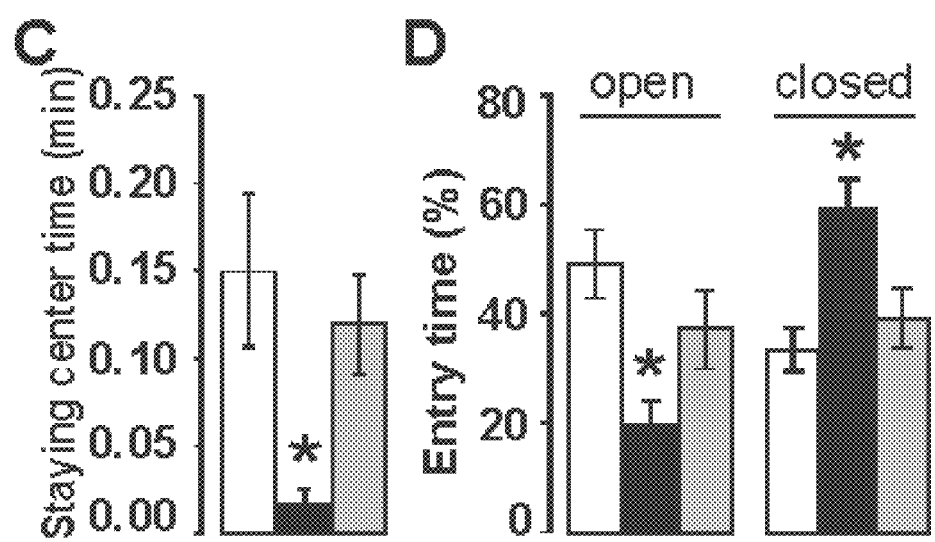

Locomotor activity was assayed with open field test. Running distance is one of the parameters quantifying locomotor activity (FIG. 4A). Wt control mice ran 882±55 cm during 10 min. TG-mice ran a much shorter distance (255±12 cm), while the running distance of TG-mice treated with D-P increased to 611±99 cm. Control mice showed frequent rearing (22.4±3.4 times), explored the center of the open field 2.0±0.6 times, and stayed at the center for 0.14±0.1 min (FIG. 4B-C). The TG-mice showed rearing 12.5±2.1 times, explored the center of the open field (0.2±0.1 times), and stayed at the center for only 0.02±0.01 min. D-P treatment in TG-mice increased rearing (19.3±2.0 times), times to explore the center (1.3±2.0 times), and duration to stay at the center (0.13±0.03 min). The results suggest that the TG-mouse of AD decreases exploratory/locomotor activity. Daily oral D-P treatment for TG-mice improves locomotor activity and increased exploring activity, an instinct of animals. Anxiety was assayed with the EPM (FIG. 4D). The wt control spent 48.5±7.5% of total time in open arms and 33.5±3.2% in closed arms. The TG-mice spent a significantly shorter time in open arms and a longer time in closed arms than those of the wt control (statistical significance vs. wt control), while the TG+D-P mice spent a similar amount of time in each arm.

These results indicate that TG-mice exhibit apathy-like behavior deficits, and anxiety. D-P treatment daily ameliorates and prevents these symptoms. These results are consistent with the notion that behavioral D-P actions involve GABAARs and that the GABAergic system contributes to behavioral changes in AD.

Oral D-P daily at dosages of 1, 10, and 100 mg/kg in a two-week study of Functional Observational Battery (FOB) in Rats did not find any notable negative changes. The results shown in Table 2 indicate that D-P is the safe compound. During the two weeks, we checked the animals' fur, response to handling, etc. All rats showed no loss of fur or negative responses to handling. No deaths or injuries were observed during the experiment. We also made sure to observe the animals continuously for 4 hours after each treatment. We mainly focused on any negative changes in the animal's mental behavior, autonomous activity, hair, glandular secretion, feces, death, etc. The FOB parameters, including body temperature, heartbeats, and breathe ratio in rats, are shown in Table 2. We found no notable changes with these evaluations.

TABLE 2

FOB parameters in male and female rats after D-P.
Temperature (T, ° C.). Pulse (P, beats/minute). Breath (B, per minute).

| Group | | day0 | day3 | day5 | day8 | | | |
|---|---|---|---|---|---|---|---|---|
| SUC | T | 36.2 ± 0.5 | 36.4 ± 0.6 | 36.3 ± 0.6 | 36.4 ± 0.5 | 36.2 ± 0.7 | 36.4 ± 0.7 | 36.3 ± 0.5 | 36.4 ± 0.6 |
| | P | 365 ± 0.3 | 365 ± 5.6 | 365 ± 3.4 | 365 ± 5.5 | 365 ± 5.8 | 365 ± 4.5 | 365 ± 7.5 | 365 ± 1.5 |
| | B | 85 ± 0.2 | 85 ± 0.4 | 85 ± 0.5 | 85 ± 0.3 | 85 ± 0.5 | 85 ± 0.5 | 85 ± 0.5 | 85 ± 0.5 |

TABLE 2-continued

FOB parameters in male and female rats after D-P.
Temperature (T, ° C.). Pulse (P, beats/minute). Breath (B, per minute).

| | | | | | | | | | |
|---|---|---|---|---|---|---|---|---|---|
| D-P | T | 36.1 ± 0.3 | 36.5 ± 0.4 | 36.4 ± 0.7 | 36.5 ± 0.3 | 36.5 ± 0.5 | 36.5 ± 1.1 | 36.4 ± 1.0 | 36.5 ± 1.2 |
| 1 | P | 367 ± 2.1 | 366 ± 1.0 | 366 ± 2.5 | 366 ± 0.4 | 366 ± 1.5 | 366 ± 1.3 | 366 ± 1.3 | 366 ± 4.1 |
| | B | 84 ± 0.3 | 85 ± 0.5 | 85 ± 0.4 | 85 ± 0.5 | 85 ± 0.5 | 85 ± 0.4 | 85 ± 0.5 | 85 ± 0.5 |
| D-P | T | 36.5 ± 0.5 | 36.3 ± 0.6 | 36.4 ± 0.6 | 36.3 ± 0.7 | 36.5 ± 0.5 | 36.3 ± 1.0 | 36.4 ± 1.1 | 36.3 ± 1.2 |
| 10 | P | 366 ± 5.2 | 367 ± 0.5 | 370 ± 0.5 | 371 ± 2.2 | 374 ± 0.5 | 369 ± 6.8 | 370 ± 1.9 | 368 ± 6.1 |
| | B | 86 ± 0.2 | 86 ± 0.6 | 86 ± 0.6 | 86 ± 0.5 | 86 ± 0.5 | 86 ± 0.5 | 86 ± 0.5 | 86 ± 0.5 |
| D-P | T | 36.4 ± 1.0 | 36.2 ± 0.7 | 36.3 ± 0.7 | 36.2 ± 0.7 | 36.4 ± 0.8 | 36.2 ± 0.7 | 36.3 ± 1.5 | 36.2 ± 0.9 |
| 100 | P | 371 ± 0.6 | 366 ± 9.5 | 365 ± 8.1 | 364 ± 0.5 | 367 ± 0.9 | 371 ± 1.5 | 365 ± 9.5 | 367 ± 1.5 |
| | B | 86 ± 0.5 | 85 ± 0.6 | 86 ± 0.3 | 85 ± 0.4 | 86 ± 0.3 | 85 ± 0.8 | 86 ± 0.5 | 85 ± 0.6 |
| | | male | female | male | female | male | female | male | female |

| Group | | day10 | | day12 | | day14 | |
|---|---|---|---|---|---|---|---|
| SUC | T | 36.2 ± 0.5 | 36.4 ± 0.6 | 36.2 ± 0.7 | 36.4 ± 0.5 | 36.2 ± 0.7 | 36.4 ± 0.7 |
| | P | 365 ± 0.3 | 365 ± 8.6 | 365 ± 0.8 | 365 ± 5.5 | 365 ± 5.8 | 365 ± 4.5 |
| | B | 85 ± 0.2 | 85 ± 0.4 | 85 ± 0.5 | 85 ± 0.3 | 85 ± 0.5 | 85 ± 0.5 |
| D-P | T | 36.5 ± 0.3 | 36.5 ± 0.4 | 36.5 ± 0.5 | 36.5 ± 0.3 | 36.5 ± 0.5 | 36.5 ± 1.1 |
| 1 | P | 366 ± 0.2 | 366 ± 1.0 | 366 ± 1.5 | 366 ± 7.4 | 366 ± 1.5 | 366 ± 6.3 |
| | B | 85 ± 0.3 | 85 ± 0.5 | 85 ± 0.5 | 85 ± 0.5 | 85 ± 0.5 | 85 ± 0.4 |
| D-P | T | 36.5 ± 0.5 | 36.3 ± 0.6 | 36.5 ± 0.5 | 36.3 ± 0.7 | 36.5 ± 0.5 | 36.3 ± 1.0 |
| 10 | P | 372 ± 6.2 | 366 ± 6.5 | 373 ± 4.5 | 367 ± 9.2 | 371 ± 7.5 | 372 ± 6.8 |
| | B | 86 ± 0.2 | 86 ± 0.6 | 86 ± 0.5 | 86 ± 0.5 | 86 ± 0.5 | 86 ± 0.5 |
| D-P | T | 36.4 ± 1.0 | 36.2 ± 0.7 | 36.4 ± 0.8 | 36.2 ± 0.7 | 36.4 ± 0.8 | 36.2 ± 0.7 |
| 100 | P | 368 ± 8.7 | 369 ± 9.5 | 371 ± 5.9 | 373 ± 6.5 | 369 ± 5.9 | 371 ± 4.5 |
| | B | 86 ± 0.5 | 85 ± 0.6 | 86 ± 0.3 | 85 ± 0.4 | 86 ± 0.3 | 85 ± 0.8 |
| | | male | female | male | female | male | female |

Figure 5:
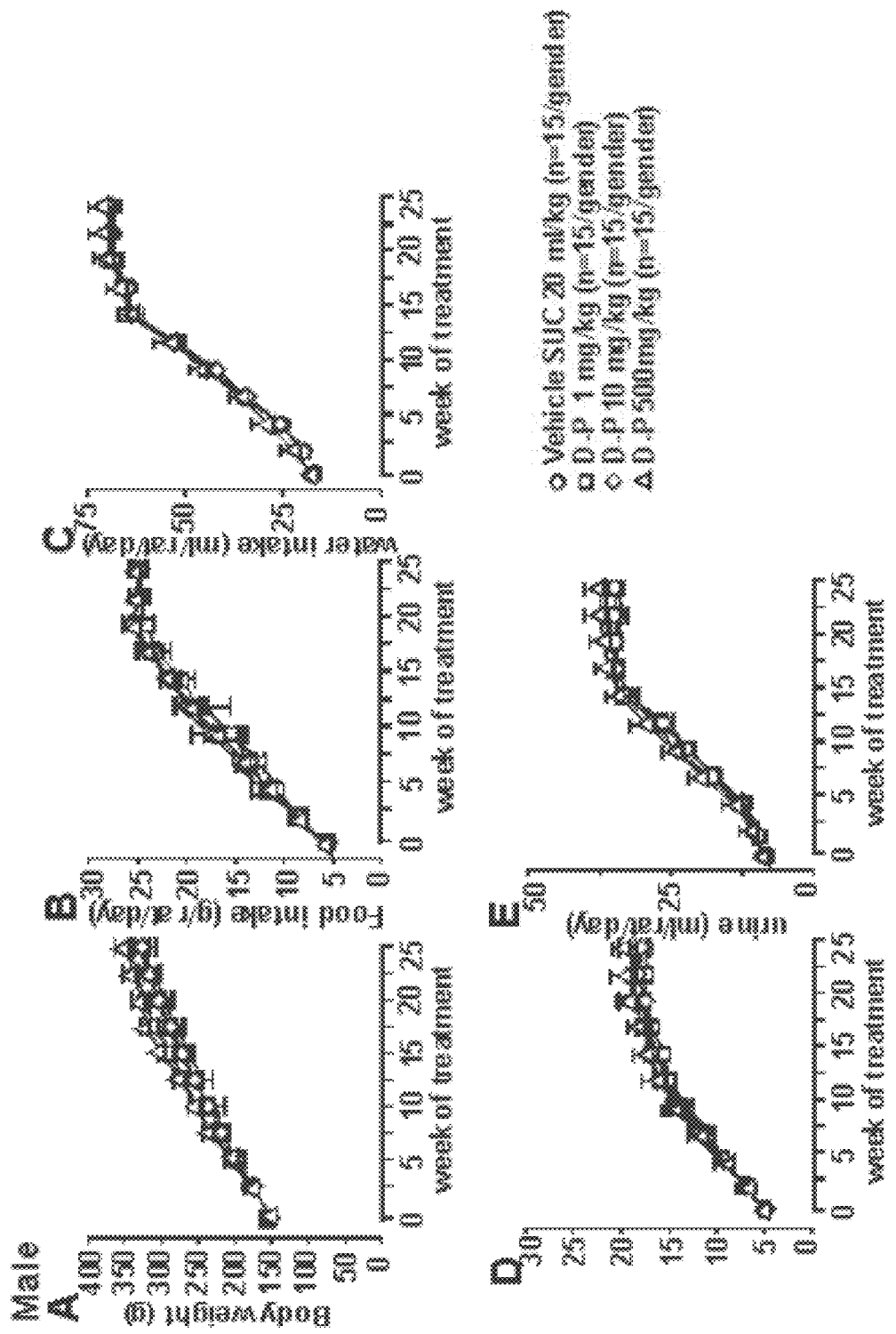
FIG. 5. A long term (six months) toxicity study of D-P evaluation in rats. Oral D-P daily at dosages of 1, 10, and 500 mg/kg in the six-month long-term evaluation study, D-P did not alter the metabolic rate.
Figure 5:
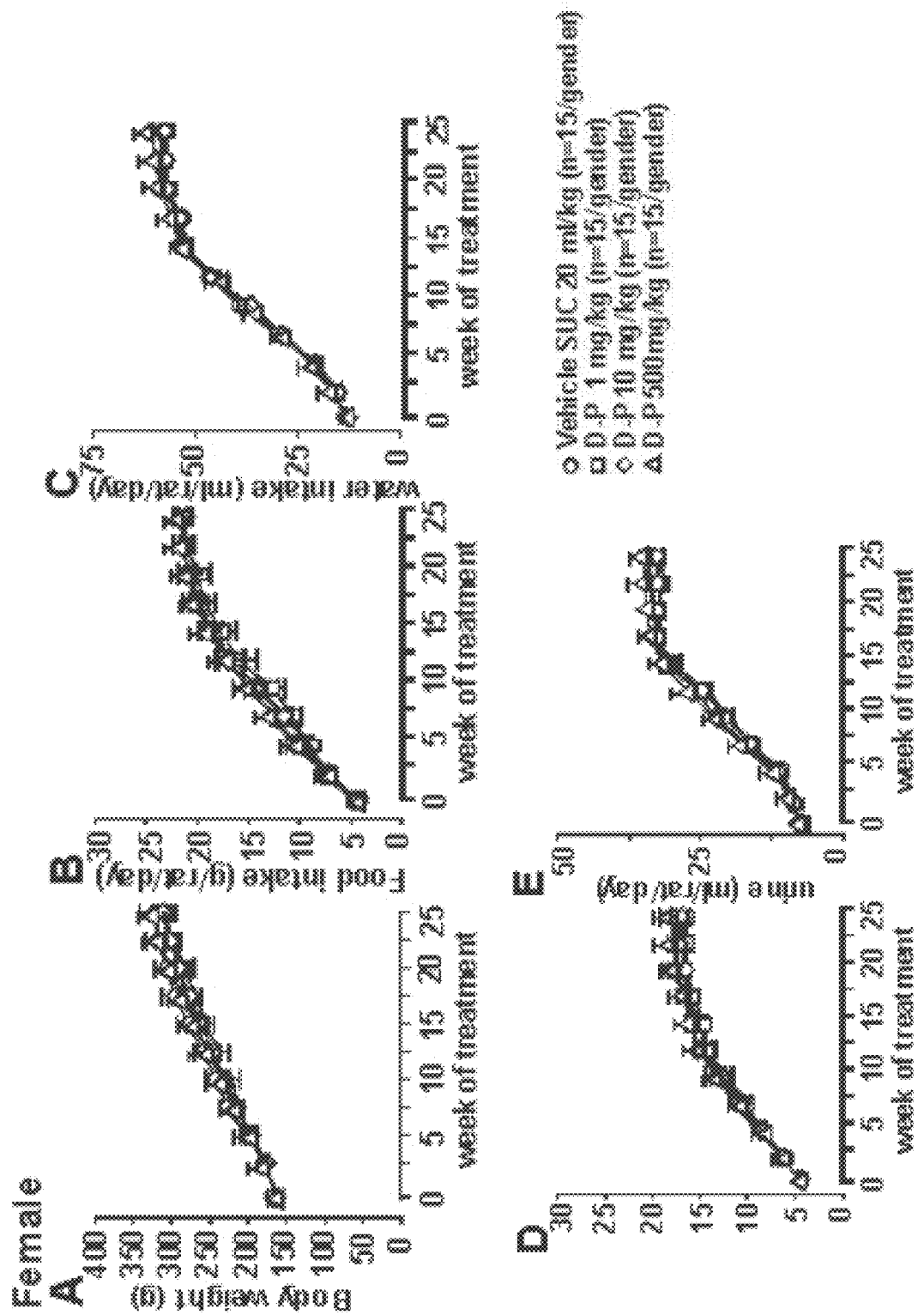

Oral D-P daily at dosages of 1, 10, and 500 mg/kg in a six-month long-term evaluation study, D-P did not alter the metabolic rate. To evaluate D-P's safety, we tested dosages of 1, 10, and 500 mg/kg (500 time high concentration) of D-P in rats. Sprague Dawley rats, male, body weight starting at 175±5 g, were used in this study. Control group rats were gavaged SUC 20 ml/kg, and D-P group rats were gavaged 1, 10, and 500 mg/kg D-P every day for six months. Compared with control group rats, D-P did not affect metabolic rates (FIG. 5). This result indicates that D-P is safe for oral everyday application without toxicity in high concentration miner.

In summary: 1) The salt-form DHM, DHM-Piperidine Complex (D-P), can maintain DHM bioavailability, increase its efficacy, and improve water solubility; 2) The salt-form DHM, DHM-Piperidine Complex (D-P) can replicate DHM effects to restore expression of gephyrin in TG animals; 3) The salt-form DHM, DHM-Piperidine Complex (D-P) can replicate DHM effects to improve cognition/memory impairment in TG-mice; 4) The salt-form DHM, DHM-Piperidine Complex (D-P) can replicate DHM effects to improve behavioral impairment in TG-mice; 5) The salt-form DHM, DHM-Piperidine Complex (D-P) is the safe compound. Oral D-P daily at dosages of 1, 10, and 100 mg/kg in a two-week study of FOB in Rats did not find any notable negative changes; and 6) The salt-form DHM, DHM-Piperidine Complex (D-P) is safe for oral everyday application without toxicity in high concentration miners. Oral D-P daily at dosages of 1, 10, and 500 mg/kg in a six-month long-term evaluation study, D-P did not alter the metabolic rate.

Figure 6:
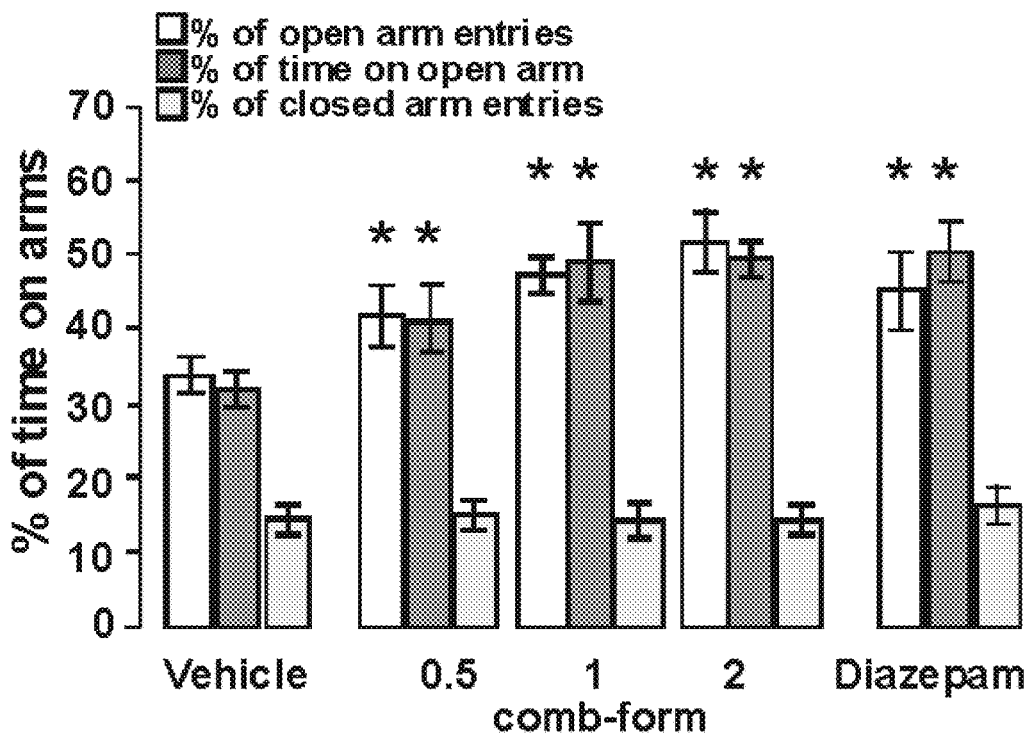
FIG. 6. Anxiolytic effect of combination-form (comb) evaluated by elevated plus maze (EPM). Effects of vehicle, comb, or diazepam presented on the behavior of mice in EPM test. Data expressed as the means (±SEM, n=7/group) percentage of open arm entries or of time spent on open arms, and the number of closed arm entries in mice given a 5-min test, 45 min after oral administration of the drugs.

Anxiolytic effect evaluation of combination form (comb). A characteristic of the anxiolytic effects of comb (0.5, 1, and 2 serving size) was evaluated by elevated plus maze (EPM) tests (Table 3; FIG. 6). The EPM is considered an etiologically valid assessment of anxiolytic/anxiety in rodents because it uses natural stimuli (fear of a novel, brightly lit open space, and fear of balancing on a relatively narrow, raised platform) to determine anxiety-like behavior in animals. Anxiolytics are known to exert their pharmacological action by causing an increase in GABAergic neurotransmission in the brain.

TABLE 3

Example of comb-ingredients in active composition for one serving size of 2 grams.

| | | |
|---|---|---|
| Hovenia | 0.625 g | 2.5% (50 mg DHM)-Extracting rate is 8%. |
| Rattan tea | 1.333 g | 10% (200 mg DHM)-Extracting rate is 15%. |
| Magnolia-vine | 1.0 g | 5% (100 mg)-Extracting rate is 10%. |
| Jujube kernels | 1.0 g | 5% (100 mg)-Extracting rate is 10%. |
| Panax Notoginseng (Leaf) | 1.0 g | 5% (100 mg)-Extracting rate is 10%. |
| Vitamin B1 | 1 mg | — |
| Vitamin B3 | 10 mg | — |
| Vitamin B6 | 1 mg | — |
| Folic acid (vitamin B9) | 0.2 mg | — |
| Vitamin B12 | 2 mg | — |

All above were in powder form and dissolved into 5% sucrose with 5% agar to make a jello or gelatin.

EPM is routinely used for the evaluation of anxiolytic activity of substances in rodent models. $GABA_4RS$ are involved in the anxiolytic effects of BZs. In this study, comb exerted significant anxiolytic effects at the dosages of 0.5, 1, 2 serving size in EPM test. Moreover, comb elicited anxiolysis, as observed in the selective increase in the number of entries and time spent on open arms. The dose-dependent increases in both the number of open arm entries and time on open arms were detected after oral administration of comb, and responses were roughly equivalent to diazepam (2 mg/kg, a typical anxiolytic dosage). That increase in total arm entries due to an increase in open arm entries correlates well with previous results. Collectively, these factors indicate the stress-alleviating effects of comb at dosages of 0.5, 1, 2 serving size.

Statistical analysis: one-way ANOVA, followed by Holm-Sidak post hoc comparison. Control versus treatment groups (comb or diazepam),*: p<0.01. Data were expressed as the means ±SEM, (n=7/group) percentage of open arm entries or of time spent on open arms in mice given a 5-min test, 45 min after oral administration of comb (0.5, 1, 2 serving size), or vehicle.

In EPM test, both comb and diazepam significantly altered the total number of arm entries with little effect in the number of closed arm entries (FIG. 6). Analysis showed that diazepam (2 mg/kg) and comb (0.5, 1, 2 serving size) significantly increased the total number of arm entries, and significantly elevated the percentage of open arm entries (p<0.01) dosage-dependently. The data indicate that combination-form of DHM has significant anxiolytic effects, similar to the dosage of diazepam to induce anxiolytic effects.

Figure 7:
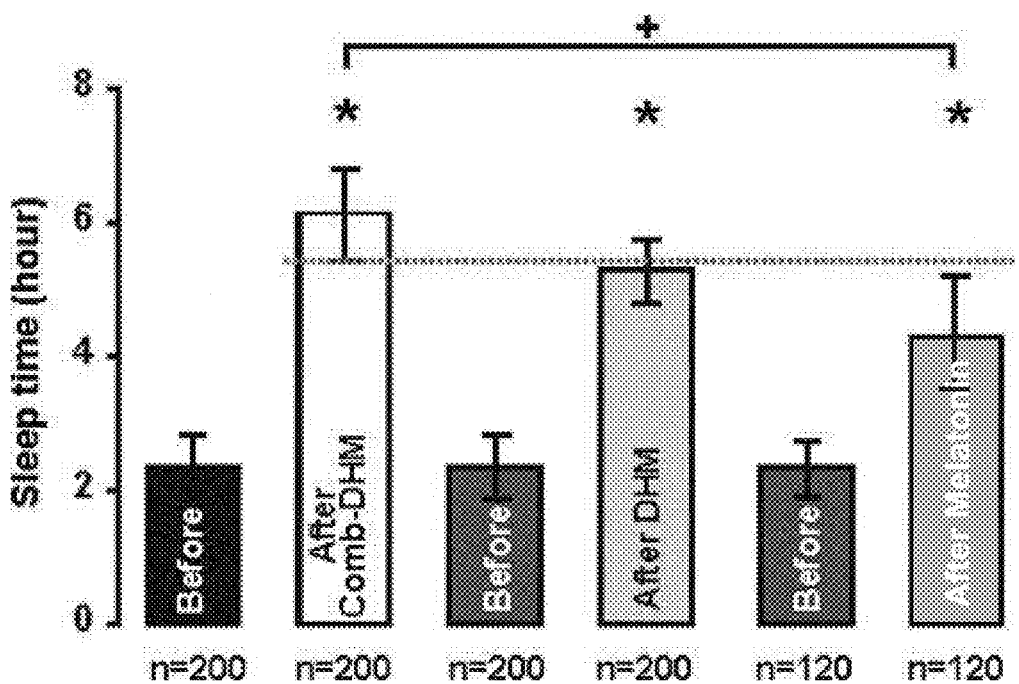
FIG. 7. Comb-form can improve the quality of sleep. Comb group received 1 serving size of comb. DHM group received 250 mg of DHM, and melatonin group received 10 mg of melatonin. Oral daily.

Combination form improves the quality of sleep and without addiction (FIG. 7). We did an Anecdotal Test of the Effects of DHM on Sleep. More than 60% of attendees were experienced melatonin users. Attendees had severe sleep problems. Their average sleep duration was about 2.5 hours/night. They were given combination-formula (Comb-D, 1 serving size), DHM (250 mg), or melatonin (10 mg). After a week, we started collecting their reported sleep duration. The Comb-D group, after taking Comb-D, had improved sleep duration, from an average of 2.4±0.65 hours to an average of 6.5±0.75 hours. The DHM group had improved sleep duration, for an average of 5.5±0.65 sleep symptoms starting between 1-7 days. Melatonin improved sleep duration to an average of 4.3±0.9 hours in 40% attendees but took a month to show this improvement in sleep. Only the melatonin group complained of dizziness on the second day, loss of energy, and other feelings of discomfort.

After finishing this three-month test, comb-group and DHM group continued having good sleep quality every day without dependence. But the melatonin-group suffered withdrawal from the test, and most participants asked for melatonin to maintain good sleep quality, indicating addiction trend or melatonin dependence.

The data indicate that the effect of promoting sleep and improving the quality of sleep from combination-form has been agreed upon by many users. The combination-form we developed is an effective combination formula with scientific data support.

In summary: 1) The combination-form can increase DHM efficacy and improve the quality of natural sleep; 2) The combination-form has significant anxiolytic effects, similar to the dosage of diazepam to induce anxiolytic effects; 3) The combination-form unlike benzodiazepines (BZs), does not induce dependence or addiction. This is very important for developing a sleep aid; 4) The combination-form does not have any negative records of safety or toxicity; 5) The combination-form not only has the effect of promoting good sleep and relaxation, but also has other health benefits, such as memory and cognition improvements, and reducing anxiety; 6) The combination-formula is a formula mixed with several extracts of herbs and selected scientifically; they display the effects on potentiating GABAAR functions tested by research.

Example 4. DHM Sleep Support Formulation for a 2-gram Serving

| Active Ingredients | | |
|---|---|---|
| *Hovenia* Extract | 50 mg | 2.5% |
| Rattan Extract | 250 mg | 12.5% (may be modified to 10 %) |
| Magnolia-Vine Extract | 100 mg | 5.0% |
| Jujube Kernels Extract | 100 mg | 5.0% |
| *Panax Notoginseng* (Leaf) Extract | 100 mg | 5.0% |
| | | Total: 30.0 % |

| Vitamins | | |
|---|---|---|
| Vitamin B1 | 1 mg | 0.05% |
| Vitamin B3 | 10 mg | 0.50% |
| Vitamin B6 | 1 mg | 0.05% |
| Folic Acid | 0.2 mg | 0.01% |
| Vitamin B12 | 2 mg | 0.10% |
| | | Total: 0.71% |

| Summary | |
|---|---|
| Active ingredients | 30.00% |
| Vitamins | 0.71% |
| Accessory Composition | 69.29% |
| Total Composition | Total: 100.00% |

| Accessory Composition (2 g Serving Size) | |
|---|---|
| Xylitol | 75.00% |
| Cellulose | 15.00% |
| Stearic Acid | 4.00% |
| Natural Color And Flavor | 2.00% |
| Silicon Dioxide | 2.00% |
| Corscarmellose Na | 1.00% |
| Magnesium Stearate | 1.00% |
| | Total: 100.00% |

We have shown that DHM, a bioflavonoid extracted from *Hovenia* or Rattan tea (vine), can counteract anxiety and depression via $GABA_A$ receptor ($GABA_AR$) activity. Further enhanced effects can be obtained by inclusion of one or more of magnolia-vine; jujube kernels, which include two types of phytochemicals, saponins and flavonoids, which trigger changes to neurotransmitters, including GABA and serotonin; including jujuboside A and spinosyn; Panax Notoginseng (Leaf); Vitamin B1; Vitamin B3, also called niacin or niacinamide; Vitamin B6; Folic acid (vitamin B9); and Vitamin B12.

Example 5. Other Formulations Comprising DHM

| Formula A | Formula B |
|---|---|
| Serving Size: 2 Capsules | Serving Size: 2 Capsules |
| DHM 98% extract 300 mg | DHM 98% extract 300 mg |
| Magnolia Vine Extract 100 mg | Magnolia Vine Extract 100 mg |
| Jujube Kernals Extract 100 mg | Jujube Kernals Extract 100 mg |
| Valerian Extract 150 mg | Valerian Extract 150 mg |
| Lemon Balm 100 mg | Lemon Balm 100 mg |
| L-Theanine 200 mg | L-Theanine 200 mg |

| Formula A | Formula B |
| --- | --- |
| Ashwagandha Ext 5% 200 mg | Ashwagandha Extract 5% 200 mg |
| — | Melatonin (Extended Release) 3 mg |
| — | Melatonin (Immediate Release) 2 mg |

TABLE 4

Certificate of Analysis of a formulation embodiment: Sleep Formula Capsules
Serving Size: 2; Beige Powder; Average Single Capsule Weight: 698 mg

| Chemical Testing/Manufacture Input per Serving: | | | |
| --- | --- | --- | --- |
| Vine tea (98% dhm) | NLT 300 mg | Input | 303 mg |
| L-theanine | NLT 200 mg | HPLC | 211.8 mg |
| Melatonin (Extended Release) | NLT 3 mg | Input | 3 mg |
| Melatonin | NLT 2 mg | Input | 2 mg |
| Ashwagandha root extract (5% Withanolides) | NLT 200 mg | Input | 202 mg |
| Valerian root extract | NLT 150 mg | Input | 151.6 mg |
| Magnolia bark extract | NLT 100 mg | Input | 101.0 mg |
| Jujube fruit extract | NLT 100 mg | Input | 101.1 mg |
| Lemon balm powder | NLT 100 mg | Input | 100 mg |
| Heavy Metal Testing: | | | |
| Arsenic | <10 µg per serving | ICP-MS | 0.144 µg per serving |
| Cadmium | <4.1 µg per serving | ICP-MS | 0.008 µg per serving |
| Lead | <0.5 µg per serving | ICP-MS | 0.161 µg per serving |
| Mercury | <0.3 µg per serving | ICP-MS | <0.005 µg per serving |
| Microbiological Testing: | | | |
| Total Plate Count | <10,000 cfu/g | AOAC 990.12 | 5 cfu/g |
| Yeast & Mold | <1000 cfu/g | AOAC 997.02 | <10 cfu/g |
| E. coli | Negative | USP <62> | Negative |
| Salmonella | Negative | USP <62> | Negative |
| S. Aureus | Negative | USP <62> | Negative |

Other Ingredients: Gelatin (optional), Magnesium Stearate, Silicon Dioxide, White Rice Flour, Titanium Dioxide (optional), FD&C Red No.3 (optional), FD&C Red No. 1 (optional).

Example 6. Clinical Trial Results

Laboratory studies have indicated that DHM is a positive modulator of $GABA^A$ receptors. GABA induces relaxation, the first stage of sleep, initiates sleep, and shuts down excitatory neurons. The inventors hypothesized that DHM's effect on GABAAR may improve the natural sleep cycle rather than forcing sleep, as some sleep medications do.

A clinical trial was performed to examine whether DHM in a combination formula with other agents could improve sleep quality among individuals classified as poor sleepers. The primary objective was to evaluate the effect of the DHM combination formula on sleep patterns in patients classified as "poor sleepers" (PSQI>5). Secondary objectives were to assess improvements in sleep quality resulting from DHM among poor sleepers and assess the safety and tolerability of the DHM combinative formula. The placebo product used in this trial was maltodextrin M100 (607 mg, 83.73 wt. %) in a size 00 gelatin capsule (16.27 wt. %).

Primary and secondary outcomes were measured using polysomnography (PSG) tests, self-report questionnaires, and patient diaries. The following endpoints were evaluated:
1. Total sleep time: The total amount of sleep time scored during the recording time—from sleep onset to sleep offset.
2. Pittsburgh Sleep Quality Index: The Pittsburgh Sleep Quality Index (PSQI) is a self-administered questionnaire to assess subjective sleep quality. It consists of 19 self-rated questions and five questions rated by one's bed partner or roommate if one is available. Only the self-rated questions were administered in this study.
3. Sleep latency: Represents elapsed time in minutes from the beginning of the PSG recording to the onset of the first 20 minutes of continuous sleep.
4. Wake After Sleep Onset (WASO): Refers to periods of wakefulness occurring after defined sleep onset.
5. Sleep efficiency: Refers to the percentage of total time in bed spent in sleep.

All analyses of within-subject changes in the efficacy variables for either treatment arm (active or placebo) were performed using paired samples t-tests and Wilcoxon signed-rank tests. Two-tailed statistical tests at the 5% significance level were conducted.

Additionally, measures of effect size (Cohen's d) and corresponding 95% confidence intervals supplemented information gleaned from statistical tests. Cohen's d measures the magnitude of an effect (effect size); values of 0.2, 0.5, and >0.8 reflect small, medium, and large effects, respectively.

A P-value can inform whether an effect exists; the P-value will not reveal the size of the effect. In reporting and interpreting studies, both the substantive significance (effect size— Cohen D test) and statistical significance (P-value) were reported.

Due to meaningful differences in the baseline characteristics of the two groups (Table 5), which would have biased the results, only intra differences of the active control arm from baseline to the last visit of the study were analyzed and reported (Table 6).

There was a statistically significant improvement in all the pre-defined sleep measures from baseline compared to the end of the study. In addition, all the pre-defined sleep measures demonstrated a large effect size.

Two AEs were reported by two participants (6.7% of the sample), all in the placebo group. AE incidence rates were 0% and 13.3% for DHM vs. Placebo groups, respectively. All reported events were categorized as mild.

TABLE 5

Characteristics of clinical trial subjects.

| | DHM | Placebo | Total |
|---|---|---|---|
| Age (yrs) | | | |
| N | 15 | 15 | 30 |
| Mean (SD) | 45.99 (10.04) | 40.65 (11.13) | |
| Median | 42.40 | 39.40 | |
| Min-Max | 31.12-65.71 | 25.31-63.40 | |
| Gender | N (%) | | |
| Male | 3 (20) | 11 (73.3) | 14 (46.7) |
| Female | 12 (80) | 4 (26.7) | 16 (53.3) |
| Race | N (%) | | |
| White | 3 (20%) | 3 (20%) | 6 (20%) |
| Black (African/African American) | 12 (80%) | 11 (73%) | 23 (76.7%) |
| Asian | 0 (%) | 1(6.7%) | 1 (3.3%) |
| Native Hawaiian/Pacific Islander | 0 (0%) | 0 (0%) | 0(0%) |
| Other | 0 (%) | 0(%) | 0 (0%) |

TABLE 6

Clinical Trial Results.

| | Baseline | | Last Visit | | Mean Diff | | Cohen's D | |
|---|---|---|---|---|---|---|---|---|
| | M | SD | M | SD | (V2-V1) | t-critical | (V2-V1) | $CI_{95}$ |
| Paired samples t-test | | | | | | | | |
| Total sleep | 336.29 | 66.54 | 399 | 34.81 | 62.71 | 3.27** | .89 | −.06, 1.47 |
| PSQI | 12.36 | 2.95 | 8.57 | 3.08 | −3.79 | −3.78** | −1.0 | −1.82, −.25* |
| Wilcoxon signed rank test | | | | | | Z-value | | |
| Latency | 61.39 | 22.63 | 24.64 | 13.89 | −36.75 | −2.70** | −1.18 | −1.76, −.19* |
| WASO | 91.46 | 50.31 | 56.39 | 30.45 | −35.07 | −2.76** | −.78 | −1.41, .11 |
| Efficiency | 68.10 | 10.92 | 83.11 | 7.24 | 15.01 | 3.11** | 1.34 | .34, 1.94* |

Example 7. Dosage Forms

The following formulations illustrate representative dosage forms that may be used for the administration of an herbal composition generally or specifically disclosed herein (hereinafter referred to as 'Composition X'). As would be readily understood by one of skill in the art, the quantities in the following compositions can be adjusted to provide compositions having higher or lower total quantities, for example, to obtain dosage forms having at least 100 mg of DHM, or about 300 mg of DHM, by adjusting the amount of each recited component proportionally.

| (i) Tablet 1 | mg/tablet |
|---|---|
| 'Composition X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Composition X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Composition X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Composition X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Composition X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Composition X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Composition X' | 5% |
| Carbomer 934 | 1.25% |
| Triethanolamine | q.s. |
| (pH adjustment to 5-7) | |
| Methyl paraben | 0.2% |
| Purified water | q.s. to 100 g |

| (viii) Topical Gel 2 | wt. % |
|---|---|
| 'Composition X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Composition X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Composition X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Composition X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A composition comprising dihydromyricetin (DHM) or a salt or complex thereof, magnolia vine extract, jujube kernels extract, *Panax notoginseng* extract, *Hovenia* extract, rattan tea extract, vitamin B1, vitamin B3, vitamin B6, vitamin B9, and vitamin B12; wherein a source of the DHM is at least one of the *Panax notoginseng* extract, the *Hovenia* extract, and the rattan tea extract; wherein the composition comprises about 5 wt. % DHM to about 40 wt. % DHM; and wherein the composition has a total weight of about 500 mg to about 2000 mg.

2. The composition of claim 1 wherein the DHM is a salt or complex that comprises an alkyl amine or an amino acid.

3. The composition of claim 1 wherein the composition further comprises melatonin, wherein the melatonin is optionally an extended time-release formulation of melatonin.

4. The composition of claim 3 wherein a weight ratio of DHM to melatonin is about 100:1, wherein the melatonin is an extended time-release formulation of melatonin; or
a weight ratio of DHM to melatonin is about 150:1, wherein the melatonin is not an extended time-release formulation of melatonin.

5. The composition of claim 3 wherein a serving of the composition comprises 3 mg±15% melatonin in an extended time-release formulation, 2 mg±15% melatonin that is not in an extended time-release formulation, or a combination thereof.

6. The composition of claim 1 wherein the DHM is stabilized against chemical degradation and its aqueous solubility is enhanced, as compared to unformulated DHM.

7. A method of treating a subject in need of neuromodulation comprising administering to the subject an effective amount of the composition according to claim 1 to provide the neuromodulation, wherein the neuromodulation aids insomnia, sleep, anxiety, or a combination of two or more thereof.

8. The method of claim 7 wherein the neuromodulation aids sleep compared to an untreated control group.

9. The method of claim 8 wherein the neuromodulation shortens the onset of sleep as compared to an untreated control group or to a group treated with only melatonin.

10. The method of claim 7 wherein the neuromodulation aids anxiety compared to an untreated control group.

11. The method of claim 7 wherein the effective amount administered is an oral dose of about 0.5 grams to about 3 grams of the composition.

12. The method of claim 7 wherein a serving of the composition has 300 mg±15% DHM, 200 mg±15% ashwagandha extract, 150 mg±15% valerian extract, 100 mg±15% magnolia extract, 100 mg±15% jujube extract, 100 mg±15% lemon balm, 200 mg±15% L-theanine, optionally 3 mg±15% melatonin in an extended time-release formulation, and optionally 2 mg±15% melatonin that is not in an extended time-release formulation.

13. The method of claim 7 wherein the effective amount is a serving of the composition administered as 1-6 individual capsules or tablets.

\* \* \* \* \*